(12) United States Patent  
Speckbacher et al.

(10) Patent No.: US 7,977,482 B2
(45) Date of Patent: Jul. 12, 2011

(54) DARK COLOURED AZO DYES

(75) Inventors: Markus Speckbacher, Aschaffenburg (DE); Jessica Chassot, Chavannes-sous-Orsonnens (CH); Hans-Jürgen Braun, Ueberstorf (CH)

(73) Assignee: The Procter & Gamble Company, Cincinnati, OH (US)

( * ) Notice: Subject to any disclaimer, the term of this patent is extended or adjusted under 35 U.S.C. 154(b) by 320 days.

(21) Appl. No.: 11/975,583

(22) Filed: Oct. 19, 2007

(65) Prior Publication Data
US 2009/0118510 A1 May 7, 2009

(30) Foreign Application Priority Data

Oct. 23, 2006 (EP) .................................... 06122740

(51) Int. Cl.
*C07D 403/06* (2006.01)
*C07D 401/12* (2006.01)
*C07D 277/20* (2006.01)

(52) U.S. Cl. ..................... 544/370; 546/209; 548/191
(58) Field of Classification Search .................. 544/370; 546/209; 548/191
See application file for complete search history.

(56) References Cited

FOREIGN PATENT DOCUMENTS

| DE | 102004051072 A1 | 4/2006 |
| DE | 102004056403 A1 | 5/2006 |
| EP | 0450438 A1 | 10/1991 |
| JP | 07-076169 | * 3/1995 |
| WO | WO-2005/117816 A1 | 12/2005 |

OTHER PUBLICATIONS

John Griffiths et al., "5-Acceptor-Substituted 4-Amino-2-Arylazothiazoles. A Unique Black Monoazo Chromophoric System," Chem. Commun. pp. 1349-1350 (1998).

Kasali A. Bello, "Long Wavelength Absorbing Azo Dyes Derived from 2-Amino-4-Chloro-5-Formylthiazole as Diazo Component," Dyes and Pigments, vol. 27(1), pp. 45-54 (1995).

Masaki Matsui et al., "Second-Order Optical Nonlinearity of Thiazolylazo Chromophores Containing Hydroxyl Groups," Dyes and Pigments, vol. 37(4), pp. 283-289 (1998).

* cited by examiner

*Primary Examiner* — James O Wilson
*Assistant Examiner* — Ebenezer Sackey
(74) *Attorney, Agent, or Firm* — Laura R. Grunzinger

(57) ABSTRACT

The present invention relates to
a) a non-oxidative coloring agent for keratin fibers, in particular human hair, comprising at least one dye according to formula (I) or (II),
b) an oxidative coloring agent for keratin fibers, in particular human hair, which comprises at least one oxidizing agent (e.g. hydrogen peroxide), at least one oxidative dye precursor and at least one dye according to formula (I) or (II), and
c) a lightening agent for keratin fibers, in particular human hair, which comprises at least one oxidizing agent (e.g. hydrogen peroxide) and at least one dye according to formula (I) or (II), with R4 being a cationic group.

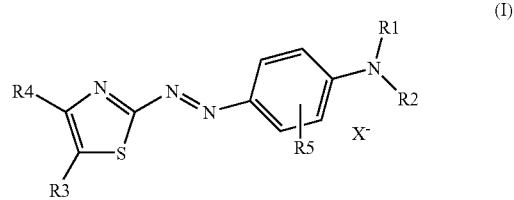

(I)

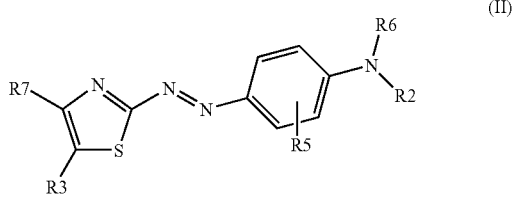

(II)

8 Claims, No Drawings

DARK COLOURED AZO DYES

FIELD OF THE INVENTION

The present invention relates to dark coloured azo dyes, preparation methods for these azo dyes and formulations for dyeing and/or lightening keratin fibres, such as, for example, human hair, wool or furs, comprising these compounds.

BACKGROUND OF THE INVENTION

In general, two processes are used for colouring keratin-containing fibres. A first method relates to the well known oxidation dyes which are formed by oxidative coupling of one or more developer components (primary intermediates) with one or more coupler components. When using oxidizing agents, however, damage to the hair structure is observed. Furthermore, some of the oxidation hair colour precursors used may have a sensitization potential. If required, oxidation-stable direct dyes can also be added to the oxidative system in order to achieve particular colour effects. Another possibility consists in the exclusive use of direct dyes. These direct dyes are used in a suitable carrier masses. This method, generally known as tinting, is easy to use, exceptionally mild and is characterized by low damage to the keratin fibres since no ammonia or peroxide is added. These dyes should meet at least some basic requirements such as durability, washing and light fastness, good toxicological and dermatological profiles and, if desired, stability towards oxidizing agents (e.g. hydrogen peroxide). A colouration system based on direct dyes often requires combinations of several dyes to obtain the desired variety of different shades. This fact is of particular interest in the case for dark colours like black shades. Normally, black shades can only be achieved by a mixture of several different direct dyes with different dyeing properties (e.g. diffusion etc.). It therefore would be desirable to have only one single black direct dye instead of a mixture of diverse direct dyes. Griffith and Riepl (Griffith/Riepl, Chem. Commun. 1998, pp 1349-1350) published a route towards black-bluish monoazo disperse dyes and their use in liquid crystal displays and optical filters. The publication in Dyes and Pigments, Vol. 27, No. 1, pp 45-54 (1995) and Dyes and Pigments, Vol. 37, No. 4, pp 283-289 (1998) disclose special 4-amino-2-arylazothiazoles which shall have a good stability and shall be superior in some cases both thermally and photochemically, relative to standard azo dyes; hair dyes are not disclosed. WO 2005/117816 A1 discloses cationic quinoxaline thiazole azo dyes and their use in colorants for keratin fibers. DE 102004056403 A1 discloses cationic pyridinylthiazo dyes and their use in colorants for keratin fibers. DE 102004051072 A1 discloses cationic heteroarylpyrazolonazo dyes and their use in colorants for keratin fibers.

SUMMARY OF THE INVENTION

An objective of the present invention is therefore to provide new dark coloured, respectively black direct dyes which are compatible to water based formulations and comply in addition to the abovementioned requirements.

Surprisingly, it has now been found that special cationic as well as anionic or neutral (uncharged) azo arrangements provide dark colours, can be applied gently to the fibres and produce naturally coloured shades. Since these dyes are also stable towards oxidizing agents (e.g. hydrogen peroxide), they can be used as well in lightening formulations or as supplement dyes in the oxidative system.

DETAILED DESCRIPTION OF THE INVENTION

Hence, the present invention relates to
a) an agent for the non-oxidative colouring of keratin fibres, in particular human hair, containing at least one dye according to formula (I) or (II),
b) an agent for the oxidative colouring of keratin fibres, in particular human hair, which comprises at least one oxidizing agent (e.g. hydrogen peroxide), at least one oxidative dye precursor and at least one dye according to formula (I) or (II), and
c) an agent for the lightening of keratin fibres, in particular human hair, which comprises at least one oxidizing agent (e.g. hydrogen peroxide) and at least one dye according to formula (I) or (II),

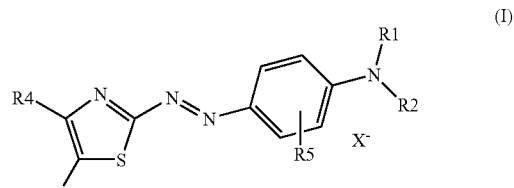

(I)

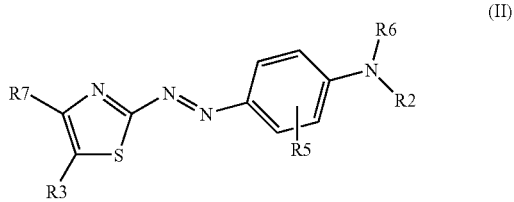

(II)

in which R1 and R2 may be identical or different and, independently of one another, are hydrogen, a benzyl group, a $C_1$-$C_6$-alkyl group, a $C_2$-$C_4$-hydroxyalkyl group, a $C_2$-$C_4$-cyanoalkyl group or a $C_4$-$C_6$-polyhydroxyalkyl group, wherein the alkyl groups can be both branched and linear; and R3 is a group according to the general formulas (III), (IV), (V), (VI) or (VII),

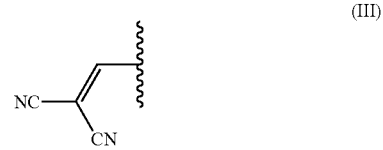

(III)

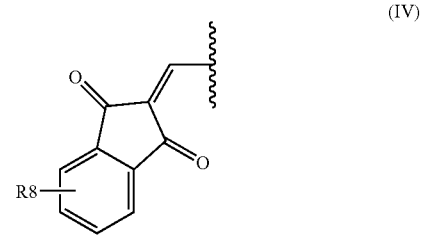

(IV)

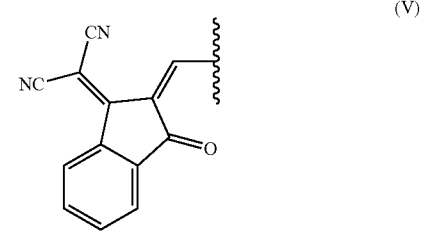

(V)

-continued

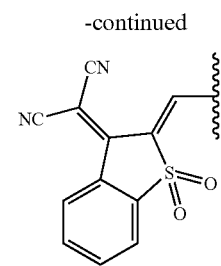
(VI)

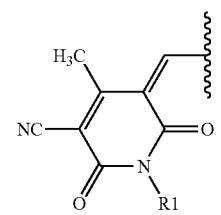
(VII)

or a formyl group, in which R8 is a hydrogen, a halogen atom, a $C_1$-$C_6$-alkyl group, or a nitro group and in which R1 has the abovementioned meaning; and R4 is a cationic group according to the general formula (VIII) or (IX),

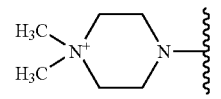
(VIII)

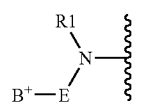
(IX)

in which E may be a $C_1$-$C_4$-alkyl group, a $C_3$-$C_6$-cycloalkyl group or an arylgroup; and R1 has the above-mentioned meaning, and $B^+$ may be a) a cationic, aromatic heterocyclic ammonium compound, preferably a cationic derivative of N-methyl-imidazole, N-allyl-imidazole, 2-ethyl-imidazole or 1,2-dimethyl-imidazole or a cationic derivative of pyridine, 4-dimethylamino-pyridine, pyrimidine, pyrazole, N-methyl-pyrazole or chinoline; or b) a non-aromatic heterocyclic ammonium compound, in particular a cationic derivative of N-methyl-morpholine, N-ethyl-morpholine or 1-methyl-piperidine; or c) a cationic alkylammonium compound or an arylammonium compound according to the formula $NR_aR_bR_c$, in which $R_a$, $R_b$ and $R_c$, independently of each other, are a benzyl rest, a phenyl rest or a $C_1$-$C_6$-alkyl rest, preferably a methyl group, an ethyl group, a propyl group, an isopropyl group or a butyl group, whereas the prementioned alkyl groups may be unsubstituted or substituted with one or more hydroxy groups or amino groups; or d) a cationic phosphonium group, e.g. a tributyl phosphonium group, preferably a trimethyl phosphonium group or a triethyl phosphonium group; and R5 is hydrogen, a halogen atom, a $C_1$-$C_6$-alkyl group, a hydroxy group, a $C_1$-$C_6$-alkyloxy group, an amino group or an amino-acetyl group; and R6 is a $C_1$-$C_6$-alkylsulfonic acid group, a $C_1$-$C_6$-alkylsulfate group (a $C_1$-$C_6$-alkylsulfonic acid ester) or their corresponding sodium or potassium salts, respectively; and R7 is a chloro atom, a pyrrolidine rest, a piperidine rest, or a N-methyl-piperazine rest or an aliphatic secondary amine rest bearing two $C_1$-$C_4$-alkyl chains which may be identical or different; and $X^-$ is a anionic counterion, preferably a sulphate anion, a methylsulphate anion, a phosphate anion, a hydrogenphosphate anion, an oxalate anion, a formate anion, an acetate anion, a citrate anion, a tartrate anion, a malonate anion, a pyruvate anion or a halogen anion, particular preference being given to the methylsulphate anion.

The dyes according to the general formula (I) or (II) are preferable chosen from

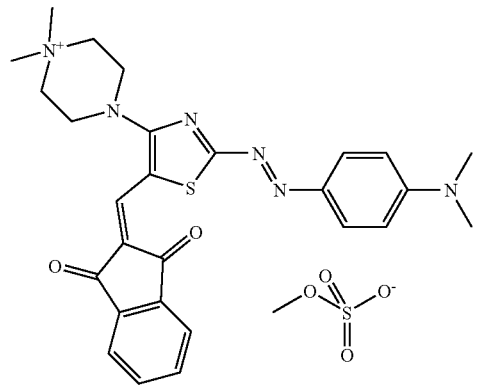

4-(2-{(E)-[4-(dimethylamino)phenyl]diazenyl}-5-[(1,3-dioxo-1,3-dihydro-2H-inden-2-ylidene)methyl]-1,3-thiazol-4-yl)-1,1-dimethylpiperazin-1-ium Methyl Sulfate (1)

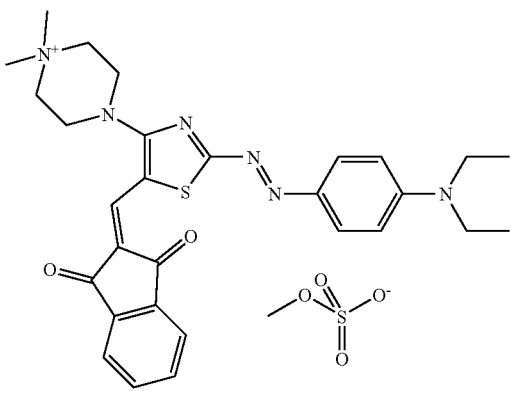

4-{2-{(E)-[4-(diethylamino)phenyl]diazenyl}-5-[(1,3-dioxo-1,3-dihydro-2H-inden-2-ylidene)methyl]-1,3-thiazol-4-yl}-1,1-dimethylpiperazin-1-ium Methyl Sulfate (2)

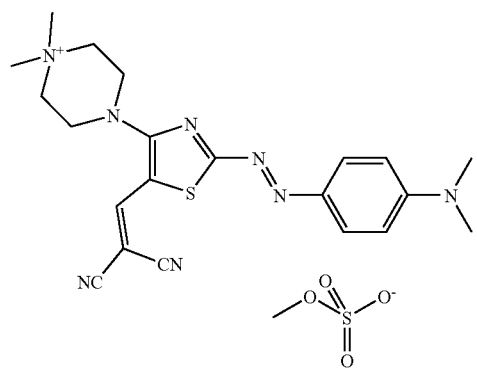

5

4-(5-(2,2-dicyanovinyl)-2-{(E)-[4-(dimethylamino)phenyl]diazenyl}-1,3-thiazol-4-yl)-1,1-dimethylpiperazin-1-ium Methyl Sulfate (3)

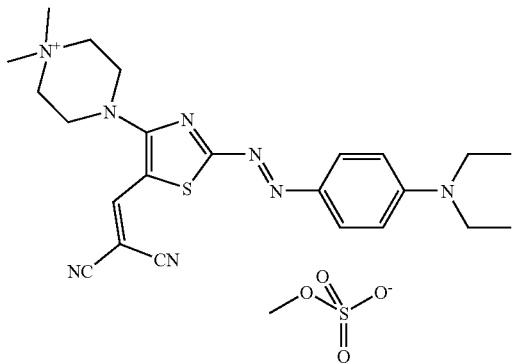

4-(5-(2,2-dicyanovinyl)-2-{(E)-[4-(diethylamino)phenyl]diazenyl}-1,3-thiazol-4-yl)-1,1-dimethylpiperazin-1-ium Methyl Sulfate (4)

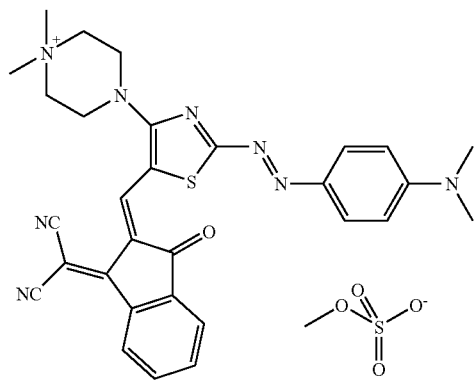

4-(5-{(Z)-[1-(dicyanomethylene)-3-oxo-1,3-dihydro-2H-inden-2-ylidene]methyl}-2-{(E)-[4-(dimethylamino)phenyl]diazenyl}-1,3-thiazol-4-yl)-1,1-dimethylpiperazin-1-ium Methyl Sulfate (5)

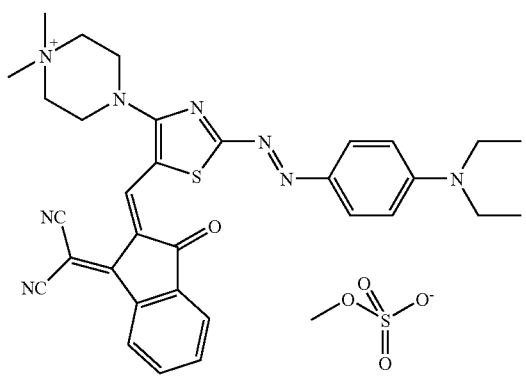

6

4-(5-{(Z)-[1-(dicyanomethylene)-3-oxo-1,3-dihydro-2H-inden-2-ylidene]methyl}-2-{(E)-[4-(diethylamino)phenyl]diazenyl}-1,3-thiazol-4-yl)-1,1-dimethylpiperazin-1-ium Methylsulfate (6)

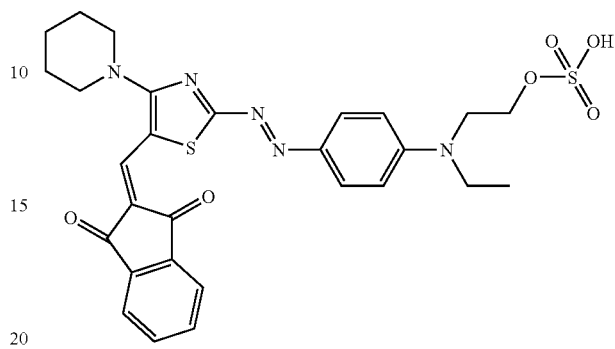

2-[{4-[(E)-{5-[(1,3-dioxo-1,3-dihydro-2H-inden-2-ylidene)methyl]-4-(1-piperidinyl)-1,3-thiazol-2-yl}diazenyl]phenyl}(ethyl)amino]ethyl Hydrogen Sulfate (7)

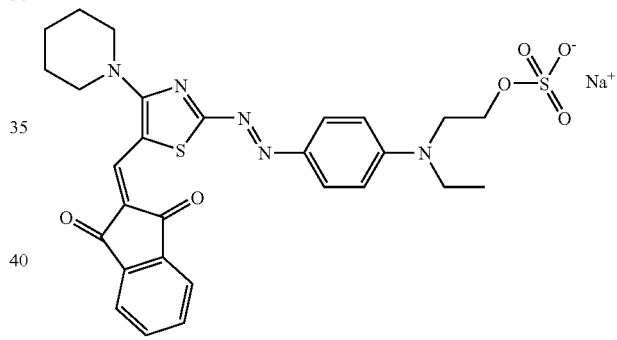

sodium 2-[{4-[(E)-{5-[(1,3-dioxo-1,3-dihydro-2H-inden-2-ylidene)methyl]-4-(1-piperidinyl)-1,3-thiazol-2-yl}diazenyl]phenyl}(ethyl)amino]ethyl Sulfate (8)

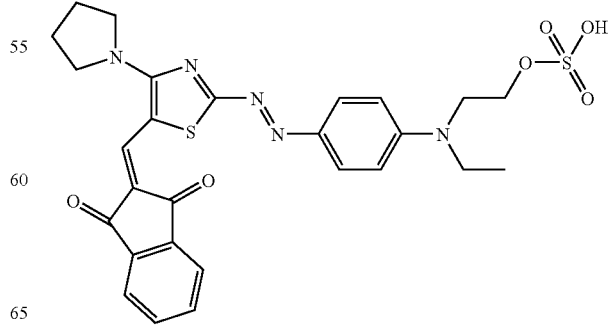

2-[{4-[(E)-{5-[(1,3-dioxo-1,3-dihydro-2H-inden-2-ylidene)methyl]-4-(1-pyrrolidinyl)-1,3-thiazol-2-yl}diazenyl]phenyl}(ethyl)amino]ethyl Hydrogen Sulfate (9)

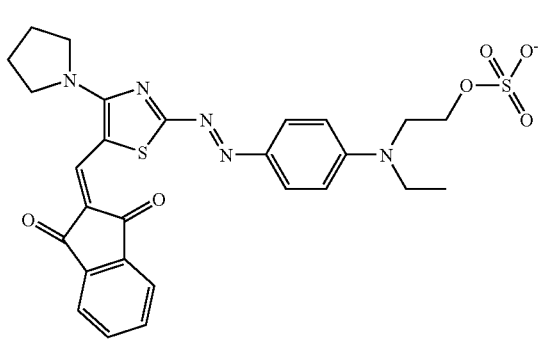

sodium 2-[{4-[(E)-{5-[(1,3-dioxo-1,3-dihydro-2H-inden-2-ylidene)methyl]-4-(1-pyrrolidinyl)-1,3-thiazol-2-yl}diazenyl]phenyl}(ethyl)amino]ethyl Sulfate (10)

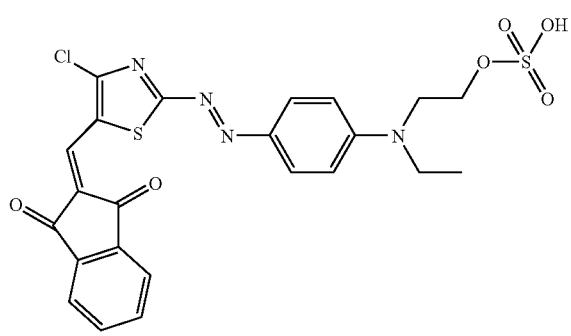

2-[{4-[(E)-{4-chloro-5-[(1,3-dioxo-1,3-dihydro-2H-inden-2-ylidene)methyl]-1,3-thiazol-2-yl}diazenyl]phenyl}(ethyl)amino]ethyl Hydrogen Sulfate (11)

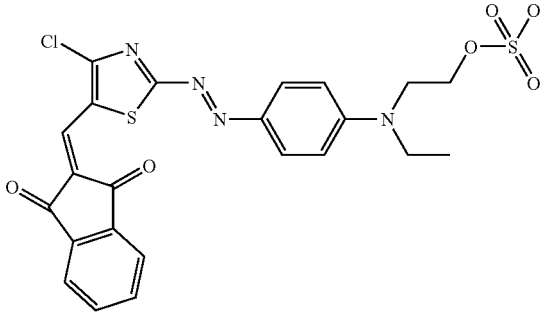

sodium 2-[{4-[(E)-{4-chloro-5-[(1,3-dioxo-1,3-dihydro-2H-inden-2-ylidene)methyl]-1,3-thiazol-2-yl}diazenyl]phenyl}(ethyl)amino]ethyl Sulfate (12)

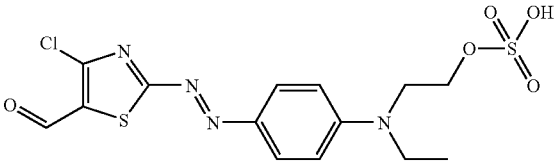

2-[{4-[(E)-(4-chloro-5-formyl-1,3-thiazol-2-yl)diazenyl]phenyl}(ethyl)amino]ethyl Hydrogen Sulfate (13)

Particularly preferred are: 4-{2-{(E)-[4-(dimethylamino)phenyl]diazenyl}-5-[(1,3-dioxo-1,3-dihydro-2H-inden-2-ylidene)methyl]-1,3-thiazol-4-yl}-1,1-dimethylpiperazin-1-ium methylsulfate, 4-{2-{(E)-[4-(diethylamino)phenyl]diazenyl}-5-[(1,3-dioxo-1,3-dihydro-2H-inden-2-ylidene)methyl]-1,3-thiazol-4-yl}-1,1-dimethylpiperazin-1-ium methylsulfate, 2-[{4-[(E)-{5-[(1,3-dioxo-1,3-dihydro-2H-inden-2-ylidene)methyl]-4-(1-piperidinyl)-1,3-thiazol-2-yl}diazenyl]phenyl}(ethyl)amino]ethyl hydrogen sulfate, 2-[{4-[(E)-{5-[(1,3-dioxo-1,3-dihydro-2H-inden-2-ylidene)methyl]-4-(1-pyrrolidinyl)-1,3-thiazol-2-yl}diazenyl]phenyl}(ethyl)amino]ethyl hydrogen sulfate, 2-[{4-[(E)-{4-chloro-5-[(1,3-dioxo-1,3-dihydro-2H-inden-2-ylidene)methyl]-1,3-thiazol-2-yl}diazenyl]phenyl}(ethyl)amino]ethyl hydrogen sulfate sulfate and 2-[{4-[(E)-(4-chloro-5-formyl-1,3-thiazol-2-yl)diazenyl]phenyl}(ethyl)amino]ethyl hydrogen sulfate.

The dyes according to the invention of the general formula (I) and (II) can be prepared via a multi-step synthesis starting with diazotation of 2-amino-4-chloro-1,3-thiazole-5-carbaldehyde (EP 0450438 A1 and Kasali A. Bello, Dyes and Pigments, Vol. 27, 1995, No. 1, 45-54) and subsequent coupling with various substituted anilines to obtain first intermediate dye derivatives, represented by structure A, in which $R_1$ and $R_2$ have the abovementioned meaning (scheme 1).

Scheme 1:

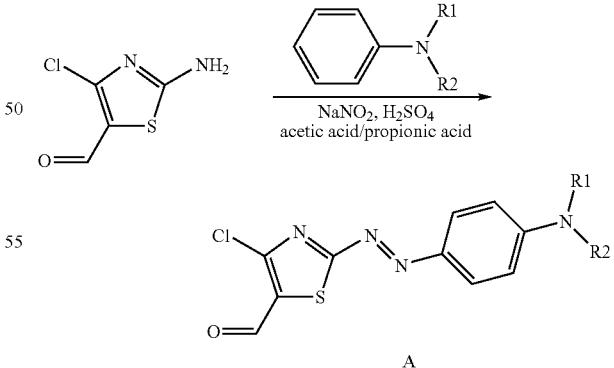

In a second step, an appropriate CH-acide acceptor-group (e.g. 1H-indene-1,3(2H)-dione) was condensed with the thiazole ring in an alcoholic medium to yield compounds according to structure B (scheme 2). This operation was performed in accordance with literature procedures (Masaki Matsui et al., *Dyes and Pigments*, Vol. 37, 1998, No. 4, 283-289).

Scheme 2:

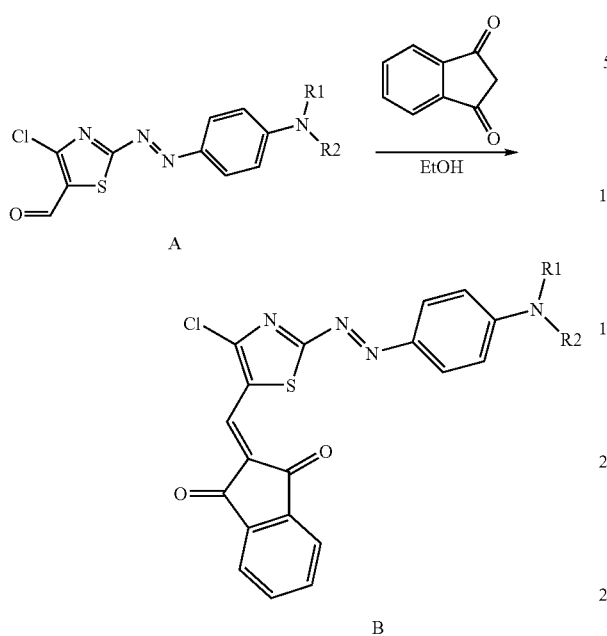

The third step involves a nucleophilic substitution of the chloro atom of B by secondary amines such as piperidine (John Griffith et al., *Chem. Commun.*, 1998, 1349-1350) or 1-methylpiperazine in solvents like THF (tetrahydrofurane) to obtain dark coloured dyes according to structure C (scheme 3).

Scheme 3:

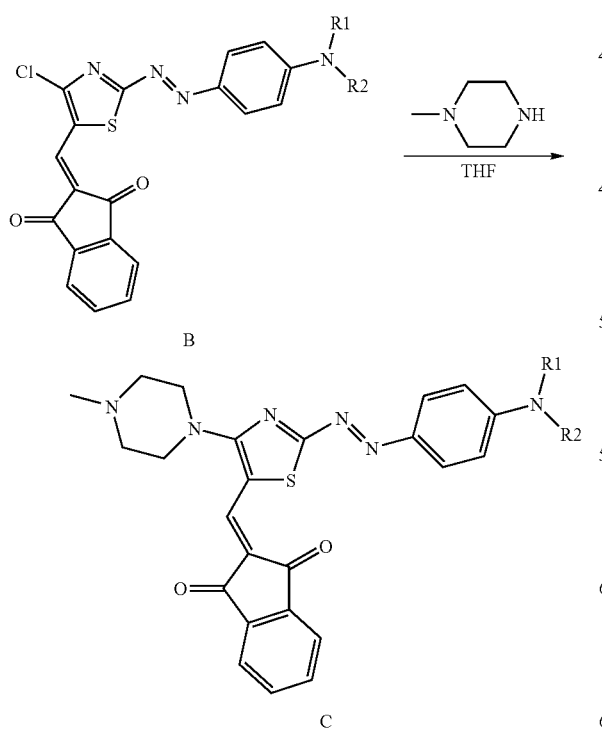

The final step, treatment of C with alkylating agents like dimethylsulfate in acetonitrile, results in the formation of desired cationic dyes (shown as D) according to the invention (scheme 4).

Scheme 4:

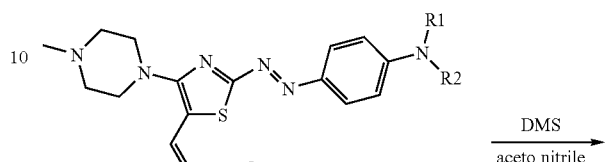

Anionic derivatives are accessible by reacting chloro sulfonic acid with an appropriate hydroxyl anchor to yield the corresponding sulfate (sulfonic acid ester) followed by conversion into an alkalimetal (e.g. sodium) salt according to the invention, if desired. However, in most cases the uncharged sulfate showed sufficient solubility. An example (designated with E, respectively E*) is illustrated in scheme 5.

Scheme 5:

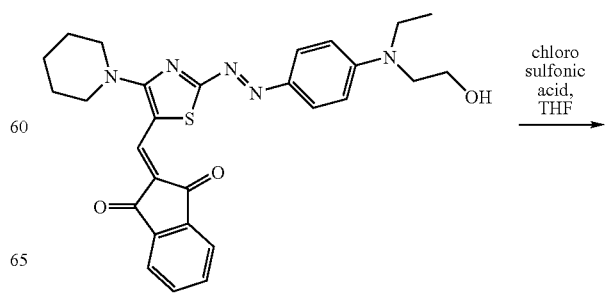

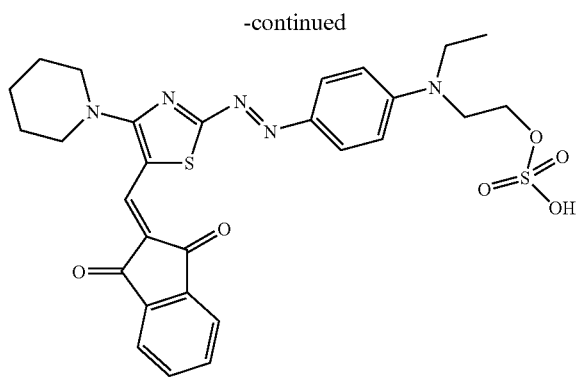

E

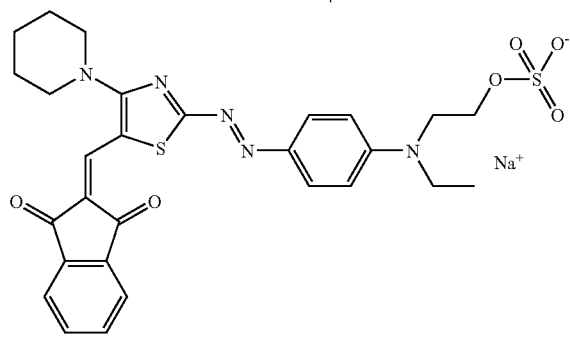

E*

Formulations, containing dyes according to the invention of the general formula (I) or (II) provide an even colouration on keratin fibres, in particular human hair, with favorable dyeing properties such as good fastness to light, washing, rubbing and perspiration. Natural colourations with low selectivity can be obtained already under gentle conditions.

The dyes of the general formula (I) or (II) according to the invention are preferably present in the colourants according to the invention in a total amount of from 0.01 to 10 percent by weight, in particular 0.1 to 8 percent by weight.

To produce special colour shades, besides the dyes of the general formula (I) or (II) according to the invention, it is possible to add to the agents according to the invention one or more additional customary direct dye from the group consisting of acidic dyes, basic dyes, nitro dyes, azo dyes, anthraquinone dyes and triphenylmethane dyes. In addition, the colourants according to the invention can also comprise naturally occurring dyes, such as, for example, henna red, henna neutral, henna black, camomile, sandalwood, black tea, buckthorn bark, sage, logwood, madder root, catechu, sedre and alkanna root.

The abovementioned additional direct dyes and naturally occurring dyes may be present in a total amount of from about 0.01 to 5 percent by weight, the total content of dyes in the colourant according to the invention being preferably from about 0.01 to 10 percent by weight, in particular 0.1 to 5 percent by weight.

The oxidative colouring system according to the invention, which is mixed with an oxidizing agent (e.g. hydrogen peroxide) prior to application, contains beside direct dyes according to formulas (I) and (II), at least one or more oxidative dye precursors (primary intermediates, coupler substances and self-coupling substances).

The abovementioned oxidative precursers may be present in a total amount of from about 0.01 to 12 percent of weight, in particular 0.2 to 6 percent by weight.

In general, lightening compositions and oxidative colouring agents according to the present invention may comprise at least one source of an oxidizing agent. Preferred oxidizing agents for use herein are water-soluble peroxygen oxidizing agents. "Water-soluble" as defined herein means that in standard condition at least 0.1 g, preferably at least 1 g, more preferably 10 g of said oxidizing agent can be dissolved in 1 liter of deionized water. The oxidizing agents are valuable for the initial solubilisation and decolourisation of the melanin (bleaching) and accelerate the oxidation of the oxidative dye precursors (oxidative dyeing) in the hair shaft. Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can also be used if desired. The oxidizing agents may be provided in aqueous solution or as a powder which is dissolved prior to use. Preferred for use in the compositions according to the present invention are hydrogen peroxide, percarbonate, persulphates and combinations thereof. According to the present invention these compositions comprise from about 0.1% to about 15% by weight, preferably from about 1% to about 10% by weight, and most preferably from about 2% to about 7% by weight of an oxidizing agent.

Another preferred oxidizing agent for use herein is a source of peroxymonocarbonate ions. Preferably such a source is formed in situ from a source of hydrogen peroxide and a hydrogen carbonate ion source.

According to the present invention the compositions may further comprise a source of radical scavenger. As used herein the term radical scavenger refers to a species that can react with a reactive radical, preferably carbonate radicals, to convert the reactive radical by a series of fast reactions to a less reactive species.

The colourants according to the invention produce natural looking colourations even at physiologically compatible temperatures of less than 45° C. They are therefore particularly suitable for colouring human hair. For use on human hair, the colourants are usually incorporated into a hydrous cosmetic carrier. Suitable cosmetic carriers are, for example, creams, emulsions, gels or else surfactant-containing foaming solutions, such as, for example, shampoos or other preparations which are suitable for application to keratin-containing fibres. If necessary, it is also possible to incorporate the colourants into anhydrous carriers, powders, pellets or granules.

The colourant according to the invention can further comprise all additives which are customary and known for such preparations, for example perfume oils, complexing agents, waxes, preservatives, polymers, thickeners, antioxidants, alginates, guar gum, haircare substances, such as, for example, cationic polymers or lanolin derivatives, or anionic, nonionic, zwitterionic, amphoteric or cationic surface-active substances (surfactants).

The abovementioned additives are used in the amounts customary for such purposes, for example the surface-active substances in a concentration of from 0.1 to 30 percent by weight, the care substances in an amount of from 0.1 to 5 percent by weight, and the polymers in a quantity of from 0.01 to 20 percent by weight.

The colourant according to the invention, particularly if it is a hair colourant, can be in the form of a powder or of granules, which is/are dissolved prior to application in an aqueous or aqueous-alcoholic preparation, or in the form of an aqueous or aqueous-alcoholic solution, a cream, a gel, an emulsion or an aerosol foam. The hair colourant according to the invention can be either in the form of a single-component preparation or in the form of a multicomponent preparation, for example in the form of a two-component preparation, where the direct dyes of the general formula (I) or (II) and other dyes (e.g. oxidative dye precursors) are packaged separately from the other ingredients (e.g. hydrogen peroxide) and the ready-to-use hair colourant is prepared immediately prior to application by mixing the two components.

The colourant according to the invention generally has a pH of from about 2 to 11, preferably about 3 to 10, in particular a neutral to basic pH from about 7 to 10 in case of direct dyes according to the general formula (I) and an acid pH from about 3 to 4 in case of direct dyes according to the general formula (II).

Both, organic and also inorganic acids are suitable for adjusting the pH according to the invention. Examples of suitable acids are the following acids: α-hydroxycarboxylic acids, such as, for example, glycolic acid, lactic acid, tartaric acid, citric acid or malic acid, ascorbic acid, gluconolactone, acetic acid, hydrochloric acid or phosphoric acid, and mixtures of these acids. Suitable alkalising media are in particular sodium carbonate, sodium bicarbonate, alkanoleamines such as monoethanoleamine or triethanoleamine, ammonia, aminopropyl-propanole and sodium hydroxide and mixtures of these bases.

The colourant according to the invention, depending on its purpose, may be applied in the presence or absence of oxidizing agents such as hydrogen peroxide.

The colourant according to the invention is generally used by applying to the hair an appropriate amount of the hair colourant, normally about 30 to 120 grams depending on the length of hair, leaving the hair colourant to act at about 15 to 45° C. for about 1 to 60 minutes, preferably 5 to 30 minutes, then thoroughly rinsing the hair with water, optionally washing with a shampoo and/or after-treating with a hair-conditioning composition and finally drying.

In addition, if no oxidizing agents are added to the colouring mass, the colourant described above can also comprise natural or synthetic polymers or modified polymers of natural origin customary for cosmetic compositions, through which setting of the hair is achieved at the same time as the colouring. Such compositions are generally referred to as tinting setting compositions or colour setting compositions. The abovementioned polymers may be present in these tinting setting compositions or colour setting compositions in the amounts customary for such compositions, in particular in an amount of from about 1 to 5 percent by weight. The pH of the colour styling foam/mousse according to the invention, is particularly of from about 6 to 9. The hair colourant with additional setting is used in a known and customary manner by wetting the hair with the setting composition, fixing (arranging) the hair in the hairstyle and then drying.

The colourant according to the invention permits an even, intense and long-lasting colouration of keratin fibres (for example human hair, wool or furs) without noteworthy discolouration of the skin and/or scalp.

The examples below are intended to illustrate the subject-matter of the invention in more detail without limiting it thereto.

EXAMPLES

Example 1

Synthesis of 4-{2-{(E)-[4-(diethylamino)phenyl]diazenyl}-5-[(1,3-dioxo-1,3-dihydro-2H-inden-2-ylidene)methyl]-1,3-thiazol-4-yl}-1,1-dimethylpiperazin-1-ium methylsulfate Step 1: Synthesis of 2-{[2-{(E)-[4-(diethylamino)phenyl]diazenyl}-4-(4-methyl-1-piperazinyl)-1,3-thiazol-5-yl]methylene}-1H-indene-1,3(2H)-dione 1.00 g (2.20 mmol) 2-[(4-chloro-2-{(E)-[4-(diethylamino)phenyl]diazenyl}-1,3-thiazol-5-yl)methylene]-1H-indene-1,3(2H)-dione and 0.30 g (2.70 mmol) 1-methylpiperazine were dissolved in 40 ml tetrahydrofurane (THF) and heated under stirring for 5 hours when thin layer chromatography (TLC) analysis indicated complete consumption of the starting material. After cooling to room temperature the formed precipitate was filtered off, washed with THF and dried in vacuum at 40° C. to obtain a dark green powder.

Yield: 0.95 g (84%)

$^1$H NMR (d$_6$-DMSO/300 MHz): δ=1.20 (t, J=6.9 Hz, 6H, 2×CH$_3$), 2.34 (s, 3H, CH$_3$), 3.01-3.04 (m, 4H, 2×CH$_2$), 3.57-3.62 (m, 4H, 2×CH$_2$), 3.84-3.86 (m, 4H, 2×CH$_2$), 6.96 (d, J=9.3 Hz, 2H, phenyl), 7.75 (s, 1H), 7.77 (s, 4H), 7.85 (d, J=9.0 Hz, 2H, phenyl).

Step 2: Synthesis of 4-[2-{(E)-[4-(diethylamino)phenyl]diazenyl}-5-[(1,3-dioxo-1,3-dihydro-2H-inden-2-ylidene)methyl]-1,3-thiazol-4-yl]-1,1-dimethylpiperazin-1-ium Methylsulfate 0.93 g (1.80 mmol) 2-{[2-{(E)-[4-(diethylamino)phenyl]diazenyl}-4-(4-methyl-1-piperazinyl)-1,3-thiazol-5-yl]methylene}-1H-indene-1,3(2H)-dione was dissolved in 20 ml acetonitrile. After addition of 0.5 g (3.70 mmol) dimethylsulfate, the mixture was heated under reflux for 24 hours. After cooling to room temperature the formed precipitate was filtered off and dried in vacuum at 40° C. to obtain a dark green solid.

Yield: 0.85 g (74%)

$^1$H NMR (d$_6$-DMSO/300 MHz): δ=1.22 (t, J=6.6 Hz, 6H, 2×CH$_3$), 2.91 (s, 3H, CH$_3$, methylsulfate), 3.29 (s, 3H, CH$_3$), 3.35 (s, 8H, 4×CH$_2$), 3.38 (s, 3H, CH$_3$), 3.62-3.64 (m, 4H, 2×CH$_2$), 7.00 (d, J=9.3 Hz, 2H, phenyl), 7.75 (s, 1H), 7.84 (s, 4H), 7.88 (d, J=9.0 Hz, 2H, phenyl).

Example 2

Synthesis of 2-[{4-[(4-chloro-5-formyl-1,3-thiazol-2-yl)diazenyl]phenyl}(ethyl)amino]ethyl Hydrogen Sulfate Step 1: Synthesis of 4-chloro-2-((E)-{4-[ethyl(2-hydroxyethyl)amino]phenyl}-diazenyl)-1,3-thiazole-5-carbaldehyde 1.3 g (18.56 mmol) sodium nitrite was added in small portions to 13.2 g conc. sulphuric acid and cooled to 0° C. and diluted with 4.8 ml propionic acid and 19.2 ml acetic acid. 3.0 g (18.45 mmol) 2-amino-4-chloro-1,3-thiazole-5-carbaldehyde were then added in small portions. The viscous reaction mixture was stirred for 2 hours at 0° C. This mixture was then added slowly to a solution of 3.2 g (18.56 mmol) 2-[ethyl (phenyl)amino]ethanol in 180 ml water, containing 6 ml sulphuric acid. After stirring for another 2 hours at room temperature, the obtained precipitate was filtered off, washed with water and dried at 40° C. in vacuum.

Yield: 3.58 g (57%)

$^1$H NMR (d$_6$-DMSO/300 MHz): δ=1.20 (t, J=6.9 Hz, 3H, CH$_3$), 3.47-3.55 (m, 6H, 3×CH$_2$), 3.96 (s, br., 1H, OH), 7.03 (d, J=9.0 Hz, 2H, phenyl), 7.84 (d, J=9.0 Hz, 2H, phenyl), 9.92 (s, 1H, formyl).

Step 2: Synthesis of 2-[{4-[(4-chloro-5-formyl-1,3-thiazol-2-yl)diazenyl]phenyl}(ethyl)amino]ethyl Hydrogen Sulfate 0.8 g (2.36 mmol) 4-chloro-2-((E)-{4-[ethyl(2-hydroxyethyl)amino]phenyl}-diazenyl)-1,3-thiazole-5-carbaldehyde were dissolved in 35 ml THF and cooled to 0° C. Then 0.28 g (2.36 mmol) chlorosulfonic acid were added slowly drop by drop with stirring. After the addition was completed, the reaction mixture was heated under reflux for 4 hours, allowed to cool to room temperature and stirred overnight. After further cooling in an ice bath the formed precipitate was filtered off, washed with a little cold THF and dried at 40° C. in vacuum.

Yield: 1.05 g (100%, containing traces of crystal water)

$^1$H NMR (d$_6$-DMSO/300 MHz): δ=1.20 (t, J=6.9 Hz, 3H, CH$_3$), 3.66-3.68 (m, 2H, CH$_2$), 3.80-3.82 (m, 2H, CH$_2$), 3.95-3.97 (m, 2H, CH$_2$), 4.77 (s, br., OH, +crystal water), 7.06 (d, J=9.0 Hz, 2H, phenyl), 7.85 (d, J=9.3 Hz, 2H, phenyl), 9.93 (s, 1H, formyl).

Example 3

Synthesis of 2-[{4-[(E)-{4-chloro-5-[(1,3-dioxo-1,3-dihydro-2H-inden-2-ylidene)methyl]-1,3-thiazol-2-yl}diazenyl]phenyl}(ethyl)amino]ethyl Hydrogen Sulfate Step 1: Synthesis of 2-{[4-chloro-2-((E)-{4-[ethyl(2-hydroxyethyl)amino]-phenyl}diazenyl)-1,3-thiazol-5-yl]methylidene}-1H-indene-1,3(2H)-dione 3.5 g (10.33 mmol) 4-chloro-2-((E)-{4-[ethyl(2-hydroxyethyl)amino]phenyl}-diazenyl)-1,3-thiazole-5-carbaldehyde and 2.33 g (15.50 mmol) 1H-indene-1,3(2H)-dione were dissolved in 90 ml ethanole and stirred under reflux. After 6 hours the mixture was allowed to cool to room temperature. The formed precipitate was filtered, washed with ethanol and dried in vacuum at 40° C. to obtain a dark powder.

Yield: 3.93 g (82%)

$^1$H NMR (d$_6$-DMSO/300 MHz): δ=1.22 (t, J=7.2 Hz, 3H, CH$_3$), 3.65-3.67 (m, 6H, 3×CH$_2$), 7.02 (d, J=9.0 Hz, 2H, phenyl), 7.78 (s, 1H), 7.84 (d, J=9.3 Hz, 2H, phenyl), 7.93 (s, 4H).

Step 2: Synthesis of 2-[{4-[(E)-{4-chloro-5-[(1,3-dioxo-1,3-dihydro-2H-inden-2-ylidene)methyl]-1,3-thiazol-2-yl}diazenyl]phenyl}(ethyl)amino]ethyl Hydrogen Sulfate 0.5 g (1.07 mmol) 2-{[4-chloro-2-((E)-{4-[ethyl(2-hydroxyethyl)amino]-phenyl}-diazenyl)-1,3-thiazol-5-yl]methylidene}-1H-indene-1,3(2H)-dione were dissolved in 50 ml THF and cooled to 0° C. Then 0.19 g (1.60 mmol) chlorosulfonic acid were added slowly drop by drop with stirring. After the addition was completed, the reaction mixture was heated under reflux for 4 hours, allowed to cool to room temperature and stirred overnight. After further cooling in an ice bath the formed precipitate was filtered off, washed with a little cold THF and dried at 40° C. in vacuum.

Yield: 0.53 g (90%)

$^1$H NMR (d$_6$-DMSO/300 MHz): δ=1.23 (t, J=6.6 Hz, 3H, CH$_3$), 3.43-3.98 (m, 6H, 3×CH$_2$), 5.65 (s, br., OH, +crystal water), 7.00 (d, J=8.7 Hz, 2H, phenyl), 7.75 (s, 1H), 7.82 (d, J=9.0 Hz, 2H, phenyl), 7.98 (s, 4H).

Example 4

Synthesis of 2-[{4-[(E)-{5-[(1,3-dioxo-1,3-dihydro-2H-inden-2-ylidene)methyl]-4-(1-piperidinyl)-1,3-thiazol-2-yl}diazenyl]phenyl}(ethyl)amino]ethyl Hydrogen Sulfate Step 1: Synthesis of 2-{[2-((E)-{4-[ethyl(2-hydroxyethyl)amino]phenyl}-diazenyl)-4-(1-piperidinyl)-1,3-thiazol-5-yl]methylene}-1H-indene-1,3(2H)-dione 0.5 g (1.07 mmol) 2-{[4-chloro-2-((E)-{4-[ethyl(2-hydroxyethyl)amino]phenyl}-diazenyl)-1,3-thiazol-5-yl]methylene}-1H-indene-1,3(2H)-dione were dissolved in 20 ml THF. Then 0.2 g (2.14 mmol) piperidine were added dropwise and the mixture was stirred under reflux for 6 hours. After cooling to room temperature, stirring was continued overnight. The formed piperidine hydrochloric salt was separated by filtration and the solvent removed with a rotary evaporator. The resulting precipitate containing the crude product was recrystallized with toluene to obtain a dark powder.

Yield: 0.36 g (66%)

$^1$H NMR (d$_6$-DMSO/300 MHz): δ=1.21 (t, J=6.6 Hz, 3H, CH$_3$), 1.65-1.74 (m, 6H, 3×CH$_2$), 3.64-3.66 (m, 6H, 3×CH$_2$), 3.83-3.85 (m, 4H, 2×CH$_2$), 4.96 (s, 1H, OH), 7.02 (d, J=9.3 Hz, 2H, phenyl), 7.75 (s, 1H), 7.76 (s, 4H), 7.87 (d, J=9.0 Hz, 2H, phenyl).

Step 2: Synthesis of 2-[{4-[(E)-{5-[(1,3-dioxo-1,3-dihydro-2H-inden-2-ylidene)methyl]-4-(1-piperidinyl)-1,3-thiazol-2-yl}diazenyl]phenyl}(ethyl)amino]ethyl Hydrogen Sulfate 0.32 g (0.62 mmol) 2-{[2-((E)-{4-[ethyl(2-hydroxyethyl)amino]phenyl}-diazenyl)-4-(1-piperidinyl)-1,3-thiazol-5-yl]methylene}-1H-indene-1,3(2H)-dione were dissolved in 33 ml THF and cooled to 0° C. Then 0.11 g (0.93 mmol) chlorosulfonic acid were added slowly drop by drop with stirring. After the addition was completed, the reaction mixture was heated under reflux for 4 hours, allowed to cool to room temperature and stirred overnight. After further cooling in an ice bath the formed precipitate was filtered off, washed with a little cold THF and dried at 40° C. in vacuum.

Yield: 0.10 g (27%)

$^1$H NMR (d$_6$-DMSO/300 MHz): δ=1.22 (t, J=6.6 Hz, 3H, CH$_3$), 1.70-1.75 (m, 6H, 3×CH$_2$), 3.67-3.69 (m, 2H, CH$_2$), 3.82-3.86 (m, 6H, 3×CH$_2$), 3.95-3.97 (m, 2H, CH$_2$), 5.57 (s, br., OH, +crystal water), 7.05 (d, J=9.0 Hz, 2H, phenyl), 7.77 (s, 1H), 7.78 (s, 4H), 7.87 (d, J=9.0 Hz, 2H, phenyl).

Example 5

| Hair Colourant | |
|---|---|
| 2.5 mmol | dye according to formula (I) |
| 5.0 g | ethanol |
| 4.0 g | decylpolyglucose |
| 0.2 g | ethylenediaminotetraacetic acid disodium salt hydrate |
| ad 100.0 g | water, demineralized |

Examples 6 to 8

| | | |
|---|---|---|
| 2.5 | mmol | dye according to formula (II) |
| 0.2 | g | 1-hydroxyethane-1,1-diphosphone acid tetrasodium salt |
| 1.3 | g | citric acid |
| 25.0 | g | ethanol |
| 10.0 | g | 1,2-propanediol |
| 9.0 | g | benzylalcohol |
| 0.5 | g | vinylpyrrolidone/vinylacetate copolymer |
| 0.4 | g | acrylic acid polymer crosslinked with a polyfunctional agent |
| ad 100.0 | g | water, demineralized |

The hair colouring for examples 5 to 8 is carried out by applying an amount of the colourant sufficient for the hair colouring to the hair and distributing it evenly using a brush. After a contact time of 30 minutes at 40° C., the hair is rinsed with lukewarm water, washed with a shampoo, rinsed with lukewarm water and then dried. In addition the dye of example 5 was also treated in the presence of hydrogen peroxide as an oxidizing agent at a basic and a neutral pH. For the second treatment 5 g of the above colour carrier mass according to example 5 were mixed with 5 g of a 6% strength hydrogen peroxide solution. For the third treatment, the pH was adjusted to a basic pH of 9 by using 25% strength ammonia. The colouring results are summarized in table 1 below.

TABLE 1

| Example No. | Compound of the formulas (I)/(II) as in example 5-8 | Colour shade after colouring | Colour measurement values after colouring |
|---|---|---|---|
| 5 | 4-{2-{(E)-[4-(diethylamino)-phenyl]diazenyl}-5-[(1,3-dioxo-1,3-dihydro-2H-inden-2-ylidene)methyl]-1,3-thiazol-4-yl}-1,1-dimethylpiperazin-1-ium methylsulfate | iron grey (without hydrogen peroxide) | L: 34.37<br>a: −0.10<br>b: −9.04 |
| | | iron grey (with hydrogen peroxide, pH = 7) | L: 38.23<br>a: +0.43<br>b: −9.99 |
| | | pale grey (with hydrogen peroxide, pH = 9) | L: 50.89<br>a: +4.83<br>b: +2.49 |
| 6 | 2-[{4-[(E)-(4-chloro-5-formyl-1,3-thiazol-2-yl)diazenyl]phenyl}(ethyl)-amino]ethyl hydrogen sulfate | intense dark blue | L: 16.71<br>a: +7.41<br>b: −10.10 |
| 7 | 2-[{4-[(E)-{4-chloro-5-[(1,3-dioxo-1,3-dihydro-2H-inden-2-ylidene)methyl]-1,3-thiazol-2-yl}diazenyl]phenyl}(ethyl)-amino]ethyl hydrogen sulfate | steel blue | L: 30.07<br>a: +4.41<br>b: −23.16 |
| 8 | 2-[{4-[(E)-{5-[(1,3-dioxo-1,3-dihydro-2H-inden-2-ylidene)methyl]-4-(1-piperidinyl)-1,3-thiazol-2-yl}diazenyl]phenyl}(ethyl)-amino]ethyl hydrogen sulfate | black | L: 18.50<br>a: −0.03<br>b: −0.78 |

Unless otherwise indicated, all percentages in the present patent application are by weight.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An agent for the non-oxidative colouring of keratin fibres, comprising at least one dye is selected from the group consisting of 4-{2-{(E)-[4-(dimethylamino)phenyl]diazenyl}-5-[(1,3-dioxo-1,3-dihydro-2H-inden-2-ylidene)methyl]-1,3-thiazol-4-yl}-1,1-dimethylpiperazin-1-ium methylsulfate, 4-{2-{(E)-[4-(diethylamino)-phenyl]diazenyl}-5-[(1,3-dioxo-1,3-dihydro-2H-inden-2-ylidene)methyl]-1,3-thiazol-4-yl}-1,1-dimethylpiperazin-1-ium methylsulfate, 4-(5-(2,2-dicyanovinyl)-2-{(E)-[4-(dimethylamino)phenyl]diazenyl}-1,3-thiazol-4-yl)-1,1-dimethylpiperazin-1-ium methylsulfate, 4-(5-(2,2-dicyanovinyl)-2-{(E)-[4-(diethylamino)phenyl]diazenyl}-1,3-thiazol-4-yl)-1,1-dimethylpiperazin-1-ium methylsulfate, 4-(5-{(Z)-[1-(dicyanomethylene)-3-oxo-1,3-dihydro-2H-inden-2-ylidene]methyl}-2-{(E)-[4-(dimethylamino)phenyl]diazenyl}-1,3-thiazol-4-yl)-1,1-dimethylpiperazin-1-ium methylsulfate, 4-(5-{(Z)-[1-(dicyanomethylene)-3-oxo-1,3-dihydro-2H-inden-2-ylidene]methyl}-2-{(E)-[4-(diethylamino)phenyl]diazenyl}-1,3-thiazol-4-yl)-1,1-dimethylpiperazin-1-ium methylsulfate.

2. An agent for the oxidative colouring of keratin fibres, comprising at least one oxidizing agent and at least one oxidative dye precursor and at least one dye is selected from the group consisting of 4-{2-{(E)-[4-(dimethylamino)phenyl]diazenyl}-5[(1,3-dioxo-1,3-dihydro-2H-inden-2-ylidene)methyl]-1,3-thiazol-4-yl}-1,1-dimethylpiperazin-1-ium methylsulfate, 4-{2-{(E)-[4-(diethylamino)-phenyl]diazenyl}-5-[(1,3-dioxo-1,3-dihydro-2H-inden-2-ylidene)methyl]-1,3-thiazol-4-yl}-1,1-dimethylpiperazin-1-ium methylsulfate, 4-(5-(2,2-dicyanovinyl)-2-{(E)-[4-(dimethylamino)phenyl]diazenyl}-1,3-thiazol-4-yl)-1,1-dimethylpiperazin-1-ium methylsulfate, 4-(5-(2,2-dicyanovinyl)-2-{(E)-[4-(diethylamino)phenyl]diazenyl}-1,3-thiazol-4-yl)-1,1-dimethylpiperazin-1-ium methylsulfate, 4-(5-{(Z)-[1-(dicyanomethylene)-3-oxo-1,3-dihydro-2H-inden-2-ylidene]methyl}-2-{(E)-[4-(dimethylamino)phenyl]diazenyl}-1,3-thiazol-4-yl)-1,1-dimethylpiperazin-1-ium methylsulfate, 4-(5-{(Z)-[1-(dicyanomethylene)-3-oxo-1,3-dihydro-2H-inden-2-ylidene]methyl}-2-{(E)-[4-(diethylamino)phenyl]diazenyl}-1,3-thiazol-4-yl)-1,1-dimethylpiperazin-1-ium methylsulfate.

3. An agent according to claim 1, further comprising at least one polymer customary for cosmetic agents, selected from the group consisting of natural polymers, synthetic polymers and modified polymers of natural origin, and is in the form of a tinting setting composition or colour setting composition.

4. An agent according to claim 2, wherein the oxidizing agent is selected from the group consisting of hydrogen peroxide and its addition compounds onto urea, melamine, sodium borate and sodium carbonate.

5. An agent according to claim 1, comprising the dye in a total amount of from 0.01 to 10 percent by weight.

6. An agent according to claim 1, additionally comprising at least one further direct dye which is selected from the group consisting of nitro dyes, azo dyes, anthraquinone dyes, triphenylmethane dyes, basic dyes, acidic dyes and naturally occurring dyes.

7. An agent according to claim 6, comprising the additional direct dye in a total amount of from 0.01 to 5 percent by weight.

8. An agent according to claim 1, comprising the dye of formula (I) and (II) in a total amount of from 0.01 to 10 percent by weight.

* * * * *